United States Patent [19]

Taylor

[11] 4,198,984
[45] Apr. 22, 1980

[54] RETAINING MEMBER FOR A CATHETER SIDE ARM

[75] Inventor: Glenn N. Taylor, Cary, Ill.

[73] Assignee: The Kendall Company, Boston, Mass.

[21] Appl. No.: 902,646

[22] Filed: May 4, 1978

[51] Int. Cl.² ............................................. A61M 25/00
[52] U.S. Cl. ............................................. 128/349 BV
[58] Field of Search ............... 128/348, 349 R, 349 B, 128/350, 351, 344, 349 BV; 24/81 CC

[56] References Cited

U.S. PATENT DOCUMENTS

| | | | |
|---|---|---|---|
| 1,478,896 | 12/1923 | Ferency | 24/81 CC |
| 2,696,963 | 12/1954 | Shepherd | 24/81 HS |
| 3,192,949 | 7/1965 | De See | 128/344 UX |

FOREIGN PATENT DOCUMENTS 560916  4/1957  Italy ....................................... 24/81 CC Primary Examiner—Harry N. Haroian
Attorney, Agent, or Firm—Powell L. Sprunger

[57] ABSTRACT

A retaining member for a conduit including a catheter having a shaft, a side arm extending from the shaft, and valve means on the side arm actuatable by contact. The retaining member has a first clip member for releasable attachment to the conduit, and a second clip member to releasably receive the catheter side arm and retain it in place relative the conduit. The second clip member has an outer tapered end for placement in the valve means and actuation thereof.

3 Claims, 4 Drawing Figures

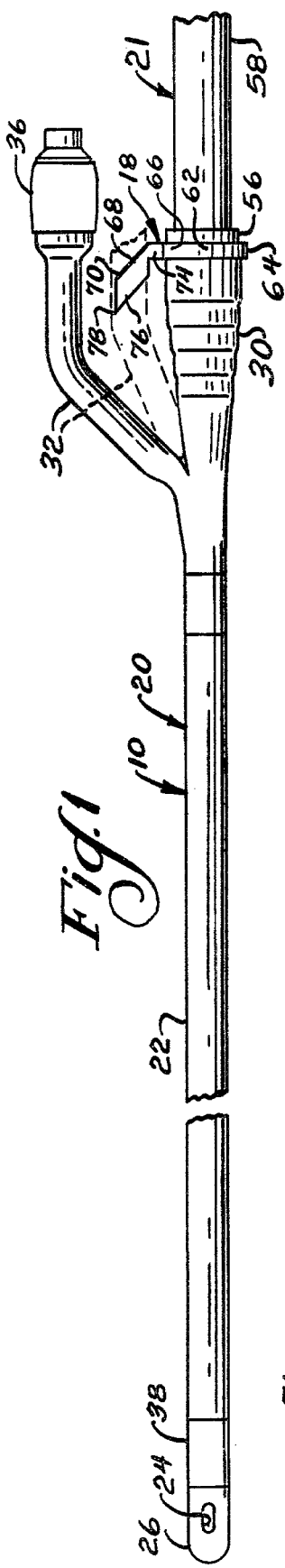
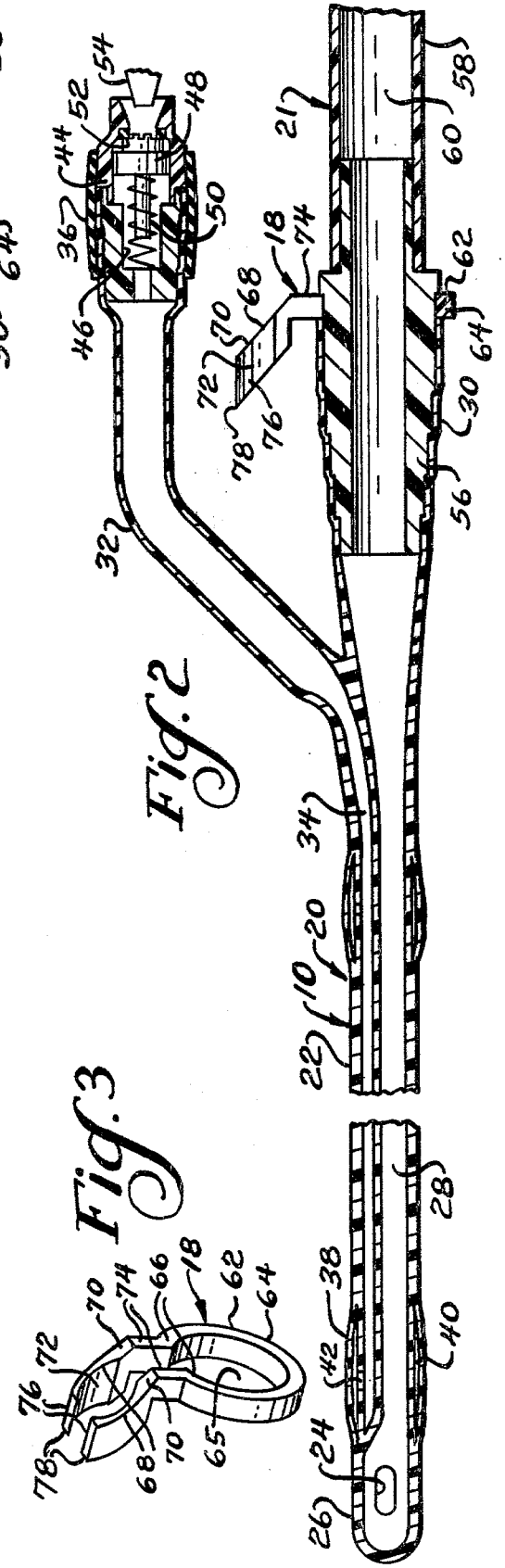
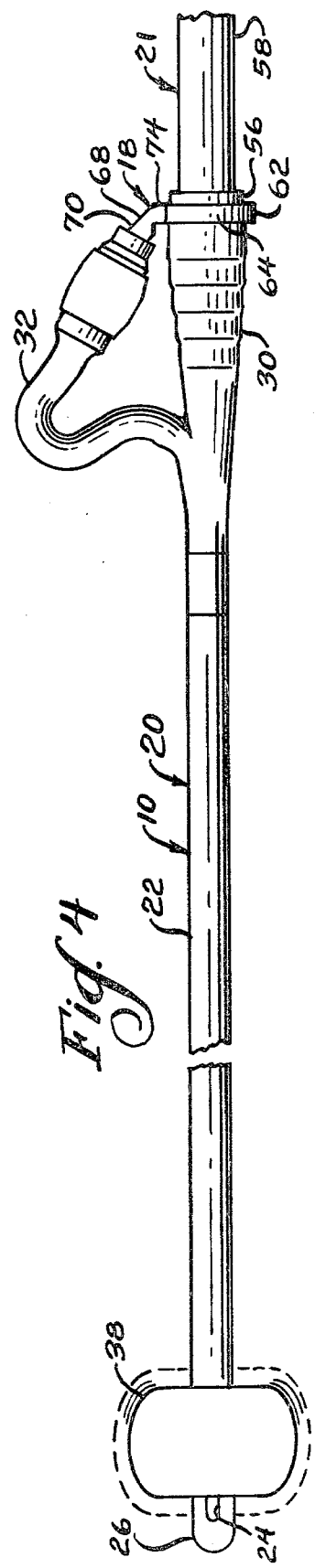

RETAINING MEMBER FOR A CATHETER SIDE ARM

BACKGROUND OF THE INVENTION

The present invention relates to catheters, and more particularly to auxiliary devices for such catheters.

In the past, a various assortment of catheters, such as Foley catheters and edotracheal tubes, have been proposed for use in patients. In the case of urinary catheters, a conventional Foley catheter is normally constructed having a shaft defining a drainage lumen extending from a drainage eye adjacent a distal end of the shaft, and an inflation lumen in the wall of the shaft extending from a valve on a side arm of the catheter to an expansible balloon overlying a distal portion of the shaft. In use, the distal end of the catheter is passed through the urethra until the drainage eye and balloon are located in the patient's bladder, and the balloon is inflated in the bladder to retain the catheter in the patient with a proximal end of the catheter located outside the patient's body. During catheterization, urine passes from the bladder through the drainage eye and lumen, and from the catheter through a drainage tube to a bag for collection therein.

Many of the valves utilized on the catheter side arms are constructed in a manner requiring physical contact to open the valves. Thus, in the normal case, the valves are designed for actuation by the tip of a syringe, such that the syringe tip is inserted into the valve to open the valve and permit passage of fluid from the syringe through the valve and side arm during inflation of the balloon. Although the valves permit simple inflation of the catheter balloon pursuant to placement of the catheter, the valves deter deflation of the balloon after catheterization has been completed, since they obstruct passage of fluid from the balloon. If a syringe is available, the attendant may deflate the balloon by inserting the tip of the syringe into the valve to actuate the valve, and by withdrawing the fluid from the balloon through the valve into the syringe. However, considerable time may have elapsed since the catheter was first placed in the patient, and a syringe may no longer be readily available. Hence, in many cases the attendant may sever the catheter side arm with an implement, such as a scissors or knife, to remove the valve and release the fluid from the catheter. In both cases an accessory device, e.g., a syringe or cutting tool, is required in order to deflate the balloon, which poses an inconvenience to hospital personnel when unavailable. Moreover, it is desirable that the catheter side arm be retained at a fixed position relative the drainage system during catheterization to prevent free movement of the side arm with respect to the catheter shaft.

SUMMARY OF THE INVENTION

A principal feature of the present invention is the provision of a retaining member for a conduit including a catheter.

The retaining member of the present invention comprises a first clip member of resilient material which is shaped to receive and engage the conduit, and a second clip member extending from the first clip member and being shaped to releasably receive a side arm of the catheter, with the second clip member having a tapered outer end.

A feature of the present invention is that the first clip member may be releasably connected to the conduit in order to secure the retaining member on the conduit.

Another feature of the invention is that the catheter side arm may be placed in the second clip member after securement of the retaining member on the conduit.

Thus, a further feature of the invention is that the retaining member maintains the side arm at a fixed position relative the conduit during catheterization.

Still another feature of the invention is that the catheter side arm may be removed from the second clip member, and the outer end of the second clip member may be placed in a valve on the side arm to actuate the valve.

Thus, a feature of the invention is that the retaining member may be utilized to open the valve and release fluid from the catheter during deflation of the balloon.

Further features will become more fully apparent in the following description of the embodiments of this invention and from the appended claims.

DESCRIPTION OF THE DRAWINGS

In the drawings:

FIG. 1 is a fragmentary elevational view of a conduit including a catheter having a retaining member of the invention positioned on the conduit;

FIG. 2 is a fragmentary sectional view of the conduit and retaining member of FIG. 1;

FIG. 3 is a perspective view of the retaining member of the present invention; and FIG. 4 is a fragmentary elevational view of the conduit illustrating use of the retaining member during deflation of a balloon on the catheter.

DESCRIPTION OF THE PREFERRED EMBODIMENTS

Referring now to FIGS. 1 and 2, there is shown a retaining member 18 for a conduit 10 comprising a liquid drainage system having a catheter 20 and drainage tube 21 which is utilized for drainage urine from the bladder of a patient. Although for convenience the present invention will be described in connection with a urinary catheter, it will be understood that the principles of the present invention are equally applicable to other suitable catheters, such as endotracheal tubes. The illustrated catheter 20 has an elongated shaft 22 having one or more drainage eyes 24 adjacent a distal end 26 of the catheter, and a main lumen 28 extending from the distal catheter end 26 to a proximal end 30 of the catheter 20. The catheter has a side arm 32 extending outwardly from the shaft 22 toward the proximal end 30 of the catheter 20, and an inflation lumen 34 extending from a valve 36 on an outer end of the side arm 32 through the side arm and the wall of the catheter shaft 22. The catheter also has an inflatable balloon 38 adjacent the distal end 26 of the catheter which defines a cavity 40 communicating through an opening 42 with the inflation lumen 34.

The valve 36 may be of conventional type such as the valve illustrated in FIG. 2. As shown, the valve 36 has a housing 44 defining a chamber 46 to receive a slidable valve element 48 which is biased by a spring 50 against a valve seat 52. Thus, the spring 50 normally retains the valve element 48 against the seat 52 in order to close the valve. The valve 36 may be actuated through a port 53 by the tip 54 of a syringe by pushing the valve element 48 away from the seat 52 to open the valve and permit passage of fluid from the syringe through the valve housing 44 and inflation lumen 34 into the balloon 38. In this manner, the balloon 38 may be inflated in the patient's bladder to retain the catheter in place in the patient. After removal of the syringe tip 54 from the valve 36, the spring 50 moves the valve element 48 against the seat 52 to close the valve and maintain the balloon in an inflated condition.

As shown in FIG. 2, the drainage tube 21 has an adapter 56 attached to a tube 58. The adapter 56 is received in the proximal end 30 of the catheter 20 in order to connect the drainage tube 21 to the catheter with a lumen 60 in the drainage tube communicating with the main lumen 28 of the catheter 20.

The retaining member 18 has a resilient first clip member 62 comprising a generally circular ring portion 64 defining an opening 65 which has an internal diameter approximately equal to or somewhat less than an outer diameter of the conduit 10, e.g., the portion of the drainage tube adapter 56 located adjacent the proximal end 30 of the catheter when the drainage tube 21 is connected to the catheter 20. The ring portion 64 has a pair of relatively closely spaced opposed ends 66, with the ring portion 64 having a sufficient length intermediate the ends 66 to extend circumferentially around a major portion of the conduit 10.

The retaining member 18 also has a second clip member 68 comprising a pair of opposed arcuate wings 70 extending radially outwardly from the ends 66 of the ring portion 64. As shown, the spaced wings 70 face each other, and define a curved passage 72 intermediate the wings 70 for a purpose which will be described below. The wings 70 are connected to the ring portion 64 by associated necks 74, and are tapered toward outer ends 76 of the wings to define associated end points 78 of the retaining member 18. The retaining member may be made of any suitable resilient material, such as polyvinylchloride or polyethylene.

During placement of the catheter, the drainage tube 21 is connected to the catheter 20, and the distal end 26 of the catheter 20 is passed through the patient's urethra until the drainage eyes 24 and balloon 38 are located in the patient's bladder with the proximal end 30 of the catheter 20 located outside the patient's body. Next, the syringe tip 54 is inserted into the valve housing 44 to actuate the valve 36 after which fluid is pumped from the syringe through the valve into the balloon 38 in order to inflate the balloon in the patient's bladder and retain the catheter in place. During catheterization, urine drains through the drainage eyes 24, the main lumen 28 of the catheter 20, and through the lumen 60 of the drainage tube 21 to a drainage bag (not shown) for collection of urine therein.

With reference to FIGS. 1–3, the ring portion 64 of the retaining member 18 is flexed in order to spread the ends 66 of the ring portion and permit passage of the conduit 10 between the wings 70 and the ring portion ends 66 until the conduit is located in the opening 65 of the ring portion 64 after which the retaining member 18 is released. In this configuration, the ring portion 64 engages an outer surface of the conduit 10, such as the drainage tube adapter 56. Thus, the retaining member 18 may be releasably secured to the conduit 10 in an orientation with the end points 78 of the wings 70 being directed along the catheter shaft 22 toward the distal end 26 of the catheter 20.

The retaining member wings 70 may then be spread slightly, and the catheter side arm 32 may be positioned in the curved passage 72 between the wings after which the wings 70 are released to permit the wings to grasp the catheter side arm, as illustrated by phantom lines in FIG. 1. Thus, the side arm 32 is releasably received between the retaining member wings 70 in order to retain the side arm in place at a fixed position relative to the conduit during catheterization.

After catheterization has been completed, the catheter side arm 32 may be removed from the retaining member wings 70 in order to free the side arm from the conduit. Next, as illustrated in FIG. 4, the side arm 32 may be flexed and either one of the wing end points 78 may be inserted into the valve port to push the valve element away from the valve seat and open the valve, thus permitting passage of fluid through the valve. In this manner, the retaining member 18 may be utilized to actuate the valve and deflate the catheter balloon 38 without the need of accessory tools, such as a syringe or cutting instrument, which may be unavailable at the time. Thus, in accordance with the present invention, the retaining member may be readily placed on the conduit in order to retain the catheter side arm at a fixed position during catheterization. After catheterization has been completed, the retaining member may be utilized in a simplified and convenient fashion to actuate the catheter valve and deflate the balloon.

The foregoing detailed description is given for clearness of understanding only, and no unnecessary limitations should be understood therefrom, as modifications will be obvious to those skilled in the art.

I claim:

1. A catheter assembly comprising,
a conduit comprising a catheter having a shaft, a side arm extending outwardly from the shaft, and valve means on the side arm actuatable by contact; and
a retaining member comprising means for securing the retaining member to the conduit, means for releasably securing the retaining member to the side arm to retain the side arm in place relative to the conduit, and means for contacting the valve means when the side arm is released from the retaining member for actuation of the valve means.

2. A catheter assembly comprising,
a conduit comprising a catheter having a shaft, a side arm extending outwardly from the shaft, and valve means on the side arm actuatable by contact; and
a retaining member comprising a first clip member of resilient material comprising a ring portion having an inside diameter approximately equal to an outside diameter of the conduit, said ring portion having a sufficient length to extend circumferentially around a major portion of the conduit, and being flexed to releasably receive the conduit such that the ring portion engages the conduit when released, and a second clip member comprising a pair of spaced arcuate wings extending outwardly from opposed ends of said ring portion to releasably receive the catheter side arm and retain it in place relative to the conduit, with at least one of said wings having a tapered outer end for placement in the valve means while the side arm is removed from the second clip member to actuate the valve means.

3. A catheter assembly comprising,
a conduit comprising a catheter having a shaft, a side arm extending outwardly from the shaft, and valve means on the side arm actuatable by contact; and
a retaining member comprising a generally circular ring portion of resilient material having an internal diameter approximately equal to an outer diameter of the conduit and a pair of relatively closely spaced opposed ends, with the ring portion being flexed for passage of the conduit between said ends and engaging an outer surface of the conduit when released to releasably secure the retaining member on the conduit, and a pair of opposed arcuate wings extending radially outwardly from the ends of said ring portion and defining a curved passge intermediate the wings to releasably receive the catheter side arm and retain it in place relative to the conduit, said wings having tapered outer ends for placement in a direction along the catheter shaft toward a distal end thereof, such that either of said wing ends may be selectively placed in the valve means for actuation of the valve means while the side arm is released from the wings.

* * * * *